United States Patent [19]

Grotta

[11] Patent Number: 4,559,182
[45] Date of Patent: Dec. 17, 1985

[54] METHOD FOR PURIFYING CRESIDINE SULFONIC ACID BY RESIN EXTRACTION

[75] Inventor: Henry M. Grotta, Delaware, Ohio

[73] Assignee: Buffalo Color Corporation, West Paterson, N.J.

[21] Appl. No.: 319,608

[22] Filed: Nov. 9, 1981

[51] Int. Cl.$^4$ ........................................... C07C 143/64
[52] U.S. Cl. ................................. 260/509; 260/505 P; 564/437; 564/438; 564/443
[58] Field of Search ....................... 564/437, 438, 443; 260/509, 505 P

[56] References Cited

U.S. PATENT DOCUMENTS 2,787,618  4/1957  McCandlish .................... 564/438 X
2,950,319  8/1960  Schenck et al. .................... 564/437
4,163,023  7/1979  Endo et al. ...................... 564/437 X

OTHER PUBLICATIONS

Rohm and Haas, "Ion Exchange with the Amberlite Resins", pp. 9-10, Nov. 1960 Ed.

Primary Examiner—Robert V. Hines
Attorney, Agent, or Firm—Michael L. Dunn; William J. Crossetta

[57] ABSTRACT

A method for removing residual cresidine from impure p-cresidine sulfonic acid which impure p-cresidine sulfonic acid contains from above two parts per billion to about 1500 parts per million of cresidine. The method comprises contacting an aqueous solution of the p-cresidine sulfonic acid with a sufficient quantity of particles of a crosslinked lipophilic porous resin for a sufficient time to reduce the concentration of p-cresidine in the cresidine sulfonic acid to less than 2 parts per billion.

6 Claims, No Drawings

METHOD FOR PURIFYING CRESIDINE SULFONIC ACID BY RESIN EXTRACTION

BACKGROUND OF THE INVENTION (A) Field of the Invention

This invention relates to the preparation of purified cresidine sulfonic acid suitable for use as an intermediate in food grade materials. More particularly, this invention relates to the removal of residual cresidine from impure cresidine sulfonic acid.

(B) History of the Prior Art

Cresidine sulfonic acid is usually prepared by sulfonation of p-cresidine to form the p-cresidine sulfate salt which rearranges to form p-cresidine sulfonic acid. p-Cresidine, also known as 2-methoxy-5-methylaniline or 5-methyl o-anisidine, is a compound known in the art which is manufactured by known procedures. One such procedure, for example, is by the reduction of 4-methyl-2-nitroanisole.

Cresidine sulfonic acid prepared by sulfonation of p-cresidine usually contains some residual cresidine. Such cresidine can be removed by established procedures to as low as a few parts per million or lower. Cresidine, however, is completely undesirable in p-cresidine sulfonic acid when the p-cresidine sulfonic acid is to be used in the manufacture of ingestible substances such as food dyes. p-Cresidine sulfonic acid is, for example, used as an intermediate in the manufacture of FDC Red No. 40.

While it has not been established that very low levels of cresidine such as one part per million cause any substantial health hazard, it is desirable to remove as much cresidine as possible from p-cresidine sulfonic acid which is used as an intermediate in the manufacture of ingestible substances since cresidine might be a potential carcinogen at higher concentrations.

In the prior art, it was not possible to remove cresidine to below detectable limits, i.e., about two parts per billion or lower.

BRIEF DESCRIPTION OF THE INVENTION

In accordance with the present invention, there is provided a method for removing residual cresidine from impure p-cresidine sulfonic acid which contains from above 2 parts per billion to about 1,500 parts per million of cresidine. The method comprises contacting the impure cresidine sulfonic acid with a sufficient quantity of particles of a crosslinked lipophylic porous resin for a sufficient time to reduce the concentrations of cresidine to less than two parts per billion.

DETAILED DESCRIPTION OF THE INVENTION

The impure p-cresidine sulfonic acid, which is purified in accordance with the method of the present invention, generally contains from above 2 parts per billion to about 1,500 parts per million of cresidine and usually contains from about 5 parts per billion to about 100 parts per million of cresidine.

The p-cresidine sulfonic acid in accordance with the present invention is contacted with a sufficient quantity of particles of a crosslinked lipopyhlic porous resin for a sufficient time to reduce the concentration of cresidine in the p-cresidine sulfonic acid to less than one part per billion. The p-cresidine sulfonic acid is contacted with the particles by any suitable method such as slurrying the particles into an aqueous solution of the p-cresidine sulfonic acid or by passing a solution of the p-cresidine sulfonic acid through a column containing the particles. In general, the sufficient time for contacting the p-cresidine sulfonic acid with the particles is from about 30 seconds to about 1 hour.

The particles of the porous resin generally have a surface area of from about 150 to about 5000 meters per gram and generally have a porosity of from about 0.2 to about 0.8 milliliters of pore per milliliter of solid in the particles.

The sufficient of quantity of resin is a weight ratio of resin to cresidine sulfonic acid of from about 0.25:1 to 1:1000 and usually from about 1:5 to 1:100.

The crosslinked lipophylic porous resin may be any suitable lipophylic porous resin; however, crosslinked porous polystyrene has been found to be particularly suitable.

Resin, which has become loaded with sufficient cresidine to become ineffective for the purpose of the method of the invention, can be cleaned by extracting the resin with a suitable solvent. Such solvents, for example, including lipophylic liquids such as liquid alkanes and ethers. A liquid which has been found suitable for cleaning absorbed cresidine from the resin is ether. The resin can be cleaned with even more efficiency by sequential washings with various mixtures of solvents. For example, the resin may first be washed with a sulfuric acid solution (e.g., a 2% solution), a wash of sodium hydroxide solution (e.g., 2.5% sodium hydroxide) and a final wash with methanol.

If desired, the impure p-cresidine sulfonic acid can be prepurified to reduce the initial concentration of cresidine to a quantity which is sufficiently low to be removed by the resin and which is desirably low enough, e.g., below one part per million, to ensure a long resin life. Prepurification methods may include contact of the cresidine sulfonic acid with sulfuric acid and steam distillation.

The following examples serve to illustrate and not limit the present invention.

EXAMPLE 1

A glass column was packed with 160 grams of Rohm and Haas Company Amberlite ® XAD-2 crosslinked polystyrene resin having a surface area of about 300 meters per gram, a porosity of between 0.40 and 0.45 milliliters of pore per milliliter of bead and an average pore diameter of from 85 to 95 angstrom units. The bed was approximately 2 cm in diameter by 50 cm in length. The column was washed with 400 milliliters of ether and then washed with water until the ether odor in the effluent was scarcely detectable.

About 1,200 milliliters of about 24% p-cresidine sulfonic acid solution containing over about 1000 parts per million cresidine based upon dry cresidine sulfonic acid was percolated through the column in 50 minutes followed by about 500 milliliters of water. The combined effluents were precipitated by addition of sulfuric acid. Cresidine sulfonic acid weighing 288.4 grams was then recovered (dry) and appeared on a UV analysis to contain no detectable cresidine. The column was then extracted with multiple alternate washings of ether and water. The ether was evaporated and the residue from the combined phases gave, on UV analysis, a concentration of 940.8 parts per million of cresidine based on p-cresidine sulfonic acid accounting for about 96% of the cresidine. The majority of the balance of the cresidine is believed to have remained in the resin since the resin was somewhat more colored after ether washing than it was originally.

EXAMPLE 2

A one liter sample of about 24% cresidine sulfonic acid solution containing somewhat over 1000 parts per million cresidine based upon cresidine sulfonic acid, was treated with sulfuric acid to precipitate the cresidine sulfonic acid which was filtered and washed with very dilute (less than 1%) sulfuric acid. Analysis of the filtrate showed a cresidine content of about 476 parts per million based upon cresidine sulfonic acid. About half of the cresidine had therefore been removed by acid washing. The p-cresidine sulfonic acid cake was then dissolved in about 1 liter of aqueous sodium hydroxide and passed through the resin column of Example 1. in about 50 minutes. Analytical examination of the effluent shows no detectable cresidine.

The highly colored resin was extracted as follows:
 (a) 2 liters of 2% sulfuric acid were passed through the column.
 (b) The column was washed with 1,700 milliliters of 2.5% sodium hydroxide solution until the effluent was neutral.

This step removed a substantial quantity of color. The column was then washed with methanol which removed most of the color from the resin.

EXAMPLE 3

A large quantity of 24% cresidine sulfonic acid solution containing slightly over 1000 parts per million cresidine based upon cresidine sulfonic acid, was precipitated with 20% sulfuric acid, washed thoroughly with 2% sulfuric acid and dried to constant weight. Upon analysis of a 51.7 gram sample, a cresidine content of 306.6 parts per million was obtained based upon cresidine sulfonic acid.

A 260.6 gram sample of the resulting p-cresidine sulfonic acid was then dissolved in a liter of distilled water by adding 50% sodium hydroxide to a pH of 10. This solution was passed through the extracted resin column of Example 2. The effluent was analyzed and determined to contain no detectable cresidine. This procedure was repeated without column regeneration using a second portion containing about 234.7 grams of cresidine sulfonic acid. Upon analysis, the second effluent was found to contain 585 parts per billion of cresidine indicating resin capacity of about 1 milligram of cresidine per gram of resin.

What is claimed is:

1. A method for removing residual cresidine from impure p-cresidine sulfonic acid which impure p-cresidine sulfonic acid contains from about 2 parts per billion to about 1500 parts per million of cresidine, said method comprising contacting an aqueous solution of the p-cresidine sulfonic acid with a sufficient quantity of particles of a crosslinked lipophilic porous resin, having a surface area of from about 150 to about 5,000 meters per gram and an average pososity of from about 0.2 to about 0.8 ml of pore per ml of solid in the particles, for a sufficient time to reduce the concentration of p-cresidine in the cresidine sulfonic acid to less than 2 parts per billion.

2. The method of claim 1 wherein the impure cresidine sulfonic acid contains from above about 5 parts per billion to about 100 parts per million of cresidine.

3. The method of claim 1 wherein the sufficient time is from about 30 seconds to one hour.

4. The method of claim 3 wherein the sufficient quantity of resin is a weight ratio of resin to cresidine sulfonic acid of from about 5:1 to 1:100.

5. The method of claim 1 wherein, prior to contact with the resin, the cresidine is steam distilled.

6. The method of claim 1 wherein the solution contains from about 10 to about 30 weight percent p-cresidine sulfonic acid.

* * * * *